United States Patent [19]

Bernstein et al.

[11] 4,129,591

[45] Dec. 12, 1978

[54] UREIDA-PHENYLENEBIS(SUBSTITUTED IMINO)MULTIANIONIC SUBSTITUTED DINAPHTHALENE SULFONIC ACIDS AND SALTS

[75] Inventors: Seymour Bernstein, New City, N.Y.; Robert H. Lenhard, Paramus, N.J.; Ransom B. Conrow, Pearl River, N.Y.

[73] Assignee: American Cyanamid Company, Stamford, Conn.

[21] Appl. No.: 736,042

[22] Filed: Oct. 27, 1976

[51] Int. Cl.$^2$ ................... C07C 143/53; A61K 31/185
[52] U.S. Cl. ................... 260/506; 260/507 R; 424/315

[58] Field of Search ........................................ 260/506

[56] References Cited

U.S. PATENT DOCUMENTS

| 1,218,655 | 3/1917 | Heymann et al. | 260/506 |
|---|---|---|---|
| 1,308,071 | 7/1919 | Heymann et al. | 260/506 |
| 1,968,820 | 8/1934 | Dyson et al. | 260/506 |

*Primary Examiner*—Nicky Chan
*Attorney, Agent, or Firm*—Claude J. Caroli

[57] ABSTRACT

Ureido-phenylenebis(substituted imino)multi-anionic substituted dinaphthalene sulfonic acids and salts, which are useful as complement inhibitors.

8 Claims, No Drawings

UREIDA-PHENYLENEBIS(SUBSTITUTED IMINO)MULTIANIONIC SUBSTITUTED DINAPHTHALENE SULFONIC ACIDS AND SALTS

SUMMARY OF THE INVENTION

The instant invention relates to novel ureidophenylenebis(substituted imino)multi-anionic substituted dinaphthalenesulfonic acids and salts and their use as complement inhibitors in warm-blooded animals.

DESCRIPTION OF THE INVENTION

This invention is concerned with compounds of the formula:

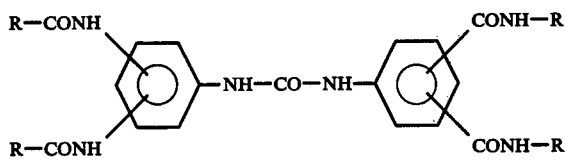

wherein R is a multi-anionic substituted naphthalene moiety of the formula:

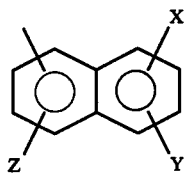

wherein X, Y and Z are selected from the group consisting of hydrogen, hydroxy, and $SO_3R_1$, wherein $R_1$ is selected from the group consisting of hydrogen, alkali metal and alkali earth metal. These novel compounds are useful as inhibitors of the complement system of warm-blooded animals.

The procedure set forth immediately below is the one by which the novel compounds of the instant invention are made. A naphthalene derivative of the formula:

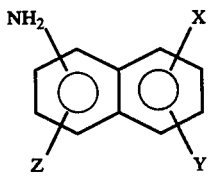

wherein X, Y and Z are as previously defined, is heated at a temperature from about 10° to about 40° C. with 5-nitro-1,3-benzenedicarbonylchloride in the presence of a sodium salt and a suitable base (e.g. sodium acetate) for several hours to obtain a dinaphthylnitrobenzene of the formula:

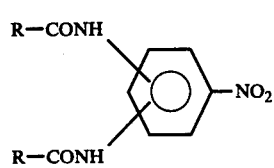

wherein R and A are as previously defined. The dinaphthylnitrobenzene solution is filtered, the filtrate concentrated in vacuo and acidified (preferably to approximately pH2) with a concentrated mineral acid (e.g. hydrochloric acid), and the product isolated by filtering after diluting with a lower alkyl alcohol. The nitro compound, in an aqueous solution, is hydrogenated at a temperature from about 10° to about 40° C. in the presence of 10% palladium on charcoal catalyst to obtain a dinaphthylaminobenzene of the formula:

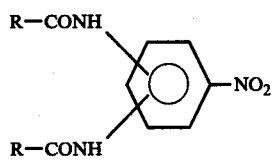

wherein R and A are as previously defined. The mixture is filtered, the filtrate concentrated in vacuo, and the product precipitated by the addition of a lower alkyl alcohol. The dinaphthylnitrobenzene compound may also be reduced chemically by warming in an aqueous solution at a temperature from about 55° to 75° C. in the presence of excess sodium sulfide nonahydrate. The solution is cooled, acidified with excess acetic acid, the mixture filtered and the product washed with a lower alkyl alcohol. An aqueous solution of the dinaphthylaminobenzene compound and a suitable base (e.g. sodium carbonate) is reacted with phosgene until the reaction is complete (as determined by thin layer electrophoresis). The solution is then concentrated in vacuo and diluted with a lower alkyl alcohol to provide the desired novel ureide.

The term "complement" refers to a complex group of proteins in body fluids that, working together with antibodies or other factors, play an important role as mediators of immune, allergic, immunochemical and/or immunopathological reactions. The reactions in which complement participates takes place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, Bull. World Health Org., 39, 935–938; (1968); Scientific American, 229, (No. 5), 54–66 (1973); Medical World News, Oct. 11, 1974, pp. 53–58; 64–66; Harvey Lectures, 66, 75–104 (1972); The New England Journal of Medicine, 287, 489–495; 545–549; 592–596; 642–646 (1972); The John Hopkins Med. J., 128, 57–74 (1971); and Federation Proceedings, 32, 134–137 (1973).

The complement system can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactons that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also invloves immune complexes. Like disseminated lupus erythematosus, it is an autoimmune disease, in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969).

A variety of substances have been disclosed as inhibiting the complement system, i.e., as complement inhibitors. For example, the compounds 3,3-(carbonyldiimino)bis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, British Journal of Experimental Pathology, 33, 327-339 (1952). The compound 8-(3-benzamido-4-methylbenzamido)naphthalene-1,-3,5-trisulfonic acid (Suramin) is described as a competitive inhibitor of the complement system, Clin. Exp. Immunol., 10, 127-138 (1972). German Patent No. 2,254,893 or South African Patent No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415-419, 902-905; 1049-1052; 1053-1056 (1969); Canadian Journal of Biochemistry, 47, 547-552 (1969); The Journal of Immunology, 93, 629-640 (1964); The Journal of Immunology, 104, 279-288 (1970); The Journal of Immunology, 106, 241-245 (1971); and The Journal of Immunology, 111, 1061-1066 (1973).

It has been reported that the known complement inhibitors 6-aminohexanoic acid, Suramin and trans-4-(aminomethyl)-cyclohexanecarboxylic acid all have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808-812 (1972).

EXAMPLE 1

8,8'-[(5-Nitro-1,3-phenylene)bis-(carbonylimino)]-bis[1,3,6-naphthalenetrisulfonic acid], hexasodium salt A mixture of 10.0 g of 5-nitro-1,3-benzenedicarboxylic acid, 50 ml of thionyl chloride and 0.2 ml of dimethylformamide is refluxed with stirring for 2½ hours. The solution is allowed to stand 48 hours at room temperature then is evaporated to an oil in vacuo. The evaporation step is repeated several times with cyclohexane and then toluene. Finally hexane is added and partial evaporation produces crystals. The mixture is cooled, then filtered. The crystals are washed with cold hexane to give 5-nitro-1,3-benzenedicarbonylchloride.

To a solution of 25.5 g of 8-amino-1,3,6-naphthalenetrisulfonic acid, trisodium salt in 100 ml of water and 60 ml of N sodium hydroxide at room temperature is added 8.13 g of 5-nitro-1,3-benzenedicarbonylchloride with about 25 ml of ether. The mixture is shaken briefly and a second 60 ml portion of N sodium hydroxide is added. The mixture is shaken for 5 minutes and a third 60 ml portion of N sodium hydroxide is added. The mixture is shaken for 15 minutes and a 1.0 g portion of the acid chloride is added with a few ml of ether, shaking is resumed for an additional 45 minutes then the mixture is acidified with 5 ml of concentrated hydrochloric acid and extracted with four 150 ml portions of ether. The aqueous solution is neutralized and is concentrated to about 50 ml in vacuo at 55° C. The remaining liquid is allowed to stand at room temperature for 48 hours and forms a solid which is diluted with 125 ml of 80% ethyl alcohol and triturated. The material is filtered and washed with 80% ethyl alcohol, absolute ethanol and ether then dried at 120° C. for a few hours. The product is then dissolved in 60 ml of water, heated on the steam bath and diluted with 300 ml of absolute ethanol. The material is filtered and washed and the final product is then dried at 120° C. overnight to give 8,8'-[(5-nitro-1,3-phenylene)bis(carbonylimino)]bis[1,-3,6-naphthalenetrisulfonic acid], hexasodium salt.

EXAMPLE 2

8,8'-[(5-Amino-1,3-phenylene)bis(carbonylimino)]-bis[1,3,6-naphthalenetrisulfonic acid], hexasodium salt.

A mixture of 28.0 g of 8,8'-[(5-nitro-1,3-phenylene)-bis(carbonylimino)]bis[1,3,6-naphthalenetrisulfonic acid], hexasodium salt, 150 ml of water and 2.3 g of 10% palladium catalyst on carbon is hydrogenated at room temperature for 5 hours at an average pressure of 43 lbs., then is filtered through diatomaceous earth and washed with water. The filtrate is then concentrated to a small volume in vacuo, absolute ethanol is added and the resulting oil is triturated until a solid is formed. This material is filtered and washed with absolute ethanol followed by ether. The product is then oven dried at 120° C. to give 8,8'-[(5-nitro-1,3-phenylene)bis(carbonylimino)bis[1,3,6-naphthalenetrisulfonic acid], hexasodium salt.

EXAMPLE 3

8,8',8'',8'''-[carbonylbis[imino-5,1,3-benzenetriylbis(carbonylimino)]]tetrakis[1,3,6-naphthalenetrisulfonic acid]

A 5.0 g portion of 8,8'-[(5-amino-1,3-phenylene)bis(carbonylimino)]bis[1,3,6-naphthalenetrisulfonic acid] hexasodium salt and 5.1 g of anhydrous sodium carbonate in 250 ml of water is phosgenated for 15 minutes. A 10.2 g portion of the sodium carbonate is added and phosgenation is continued for 15 minutes. The solution is neutralized with 5.1 g of the sodium carbonate and concentrated in vacuo at 55° C. until sodium carbonate precipitates. The solution is decanted and the concentration repeated twice. Finally the solution is evaporated to dryness and the residue is boiled with 100 ml of methanol. The methanol solution and the methanol insoluble residue are combined and dissolved in 50 ml of water. This solution is acidified to Congo Red with 5 ml of concentrated hydrochloric acid and then evaporated at 68°-70° C. in vacuo to dryness. The residue is extracted with 100 ml of hot dimethylformamide, filtered and washed with 30 ml of dimethylformamide. The filtrate and washings are combined and evaporated in vacuo at 70° C. and then re-evaporated from benzene. The residue is heated in 50 ml of absolute ethanol and triturated until filterable. It is then filtered and washed with ether. The solid is dissolved in 10 ml of water, heated on a steam bath and then diluted with 70 ml of absolute ethanol, filtered and washed with absolute ethanol and ether. The solid is dissolved in 2 ml of water, heated on a steam bath, diluted gradually with 6 ml of methanol and then diluted gradually with 65 ml of acetone. The mixture after standing at room temperature overnight is filtered and washed with acetone and ether, giving the product 8,8',8'',8'''[carbonylbis[imino-5,1,3-benzenetriylbis(carbonylimino)tetrakis][1,3,6-naphthalenetrisulfonic acid].

Treatment of the above product with aqueous sodium acetate provides the dodecasodium salt. Similarly, treatment with aqueous potassium acetate provides the dodecapotassium salt, and treatment with aqueous calcium acetate provides the calcium salt.

EXAMPLE 4

8,8',8'',8'''-[Carbonylbis[imino-5,1,3-benzenetriylbis(carbonylimino)]]tetrakis[1,3,6-naphthalenetrisulfonic acid]dodecasodium salt A 4.5 mmole portion of 8,8'-[(5-amino-1,3-phenylene)-bis(carbonylimino)]bis[1,3,6-naphthalenetrisulfonic acid] hexasodium salt is dissolved in 25 ml of water plus 4.0 ml of pyridine. Phosgene is passed into this solution until it is acidic. A 0.5 ml portion of pyridine is added and phosgene is again passed through the solution until it is acidic. Another 0.5 ml of pyridine is added to make the solution weakly basic. The solution is poured into 250 ml of ethanol, filtered and washed with ethanol and ether giving a pink powder. The product is added to 20 ml of water and the pH is adjusted to 8.0 with 5N sodium hydroxide. The solution is diluted with 200 ml of ethanol, stirred for one hour and filtered. The solid is washed with ethanol and ether and then dried overnight at 110° C. giving 4.70 g of the product as a tan powder.

EXAMPLE 5

8,8'-[(5-Nitro-1,3-phenylene)bis(carbonylimino)]-bis[1,3,5-naphthalenetrisulfonic acid] hexasodium salt To a mixture of 26.6 g of 8-amino-1,3,5-naphthalenetrisulfonic acid in 25 ml of water is added 12 ml of 5N sodium hydroxide. This solution is added to 125 ml of ethanol and stirred for 30 minutes. The resulting solid is recovered by filtration, washed with 50 ml of 80% ethanol followed by ethanol and ether and dried at 110° C. giving 8-amino-1,3,5-naphthalenetrisulfonic acid trisodium salt.

To a solution of 18.0 g of the above product and 5.9 g of sodium acetate trihydrate in 100 ml of water is added 5.2 g of 5-nitro-1,3-benzenedicarbonylchloride. The mixture is stirred for 1¾ hours, then treated with activated carbon and filtered through diatomaceous earth. The filtrate is concentrated to about 75 ml and acidified with 1.0 ml of concentrated hydrochloric acid. The solution is diluted with 500 ml of ethanol and stirred for 1 hour. The solid which forms is filtered, washed with 87% ethanol followed by ethanol and ether and dried overnight at 110° C. The solid is dissolved in 75 ml of water, filtered and the filtrate is diluted with 400 ml of ethanol with vigorous stirring for 10 minutes. The solid which forms is filtered, washed with 85% ethanol followed by ethanol and ether and dried at 110° C. giving 8,8'-[(5-nitro-1,3-phenylene)bis(carbonylimino)]bis[1,3,5-naphthalenetrisulfonic acid] hexasodium salt.

EXAMPLE 6

8,8'-[(5-Amino-1,3-phenylene)bis(carbonylimino)]-bis[1,3,5-naphthalenetrisulfonic acid] hexasodium salt A 16.0 g portion of 8,8'-[(5-Amino-1,3-phenylene)-bis(carbonylimino)]bis[1,3,5-naphthalenetrisulfonic acid] hexasodium salt and 1.0 g of palladium on carbon catalyst in 100 ml of water is hydrogenated for one hour. The mixture is filtered through diatomaceous earth and the filtrate is concentrated to 50 ml. This solution is diluted with 400 ml of ethanol giving an oil and a colorless suspension. The suspension is decanted and filtered through diatomaceous earth. The product is recovered by washing the diatomaceous earth with water. This aqueous solution is concentrated to a small volume and diluted with ethanol giving an oil which is combined with the first oil and stirred with absolute ethanol until the oil solidifies. The solid is ground, washed with ethanol and ether and dried at 110° C. giving 8,8'-[(5-amino-1,3-phenylene)bis(carbonylimino)bis[1,3,5-naphthalenetrisulfonic acid] hexasodium salt.

EXAMPLE 8

4,4'-[5-Amino-1,3-phenylenebis(carbonylimino)]bis[2,7-naphthalenedisulfonic acid] tetrasodium salt.

Approximately 76 g. of 1-amino-3,6-naphthalenedisulfonic acid is added to a solution of 22 g of sodium hydroxide in 100 ml of water. This solution is treated with charcoal filtered through diatomaceous earth and washed with sufficient water to bring the combined filtrate and washings to 200 ml. The filtrate is diluted to 1000 ml with ethanol and after standing the resulting solid is filtered and washed with absolute ethanol and twice with ether. The product is dried overnight giving 1-amino-3,6-naphthalenedisulfonic acid disodium salt.

A mixture of 23.0 g of the above aminocompound and 5.5 g of sodium acetate is diluted with 200 ml of water. A 7.82 g portion of 5-nitro-1,3-benzenedicarbonylchloride is added. The reaction mixture is stirred for 100 minutes and reduced to less than 100 ml on a rotary evaporator. This solution is adjusted to pH 1-2 with one ml of concentrated hydrochloric acid, treated with charcoal and diluted to 100 ml with water. The solution is heated on a steam bath and 150 ml of absolute ethanol is added. Cooling produces a solid which is filtered and washed with two 50 ml portions and 70% ethanol and then with two 50 ml portions of absolute ethanol and finally with 2 portions of ether. The filtrate minus the ether washes is diluted with 200 ml of absolute ethanol and dried in an oven for 48 hours. This material and 1.5 g of 10% palladium on carbon catalyst in 100 ml of water are shaken in an atmosphere of hydrogen at an initial pressure of 40 psi for 3½ hours. The reaction mixture is filtered through diatomaceous earth. The filtrate is reduced in volume on a rotary evaporator until a solid precipitates. The solid is filtered, washed with two 25 ml portions of 50% ethanol, then with absolute ethanol and finally with two portions of ether and dried in vacuo overnight giving 4,4'-[5-amino-1,3-phenylenebis(carbonylimino)]bis[2,7-naphthalenedisulfonic acid] tetrasodium salt.

EXAMPLE 9

4,4',4'',4'''-{Carbonylbis[imino-5,1,3-benzenetriylbis(carbonylimino)]}tetrakis[2,7-naphthalenedisulfonic acid] octasodium salt A 6.70 g portion of 4,4'-[5-amino-1,3-phenylenebis(carbonylimino)]bis[2,7-naphthalenedisulfonic acid] tetrasodium salt is dissolved in 110 ml of water. A 2.23 g portion of sodium carbonate is added. Phosgene is led into the reaction for 15 minutes. The reaction mixture is filtered and then reduced in volume to about 50 ml on a rotary evaporator. The solution is basified with 5N sodium hydroxide. The addition of 100 ml of absolute ethanol produces a solid which is washed with two 25 ml portions of 70% ethanol, two portions of absolute ethanol and finally with two portions of ether and then dried in vacuo. This solid is taken up in hot water and absolute ethanol is added until a solid precipitates. This mixture is cooled and the solid is collected and washed as before and dried in vacuo. This solid is suspended in 100 ml of absolute ethanol and boiled on a steam bath. Water is slowly added until solution occurs. The solution is treated with charcoal and on cooling a solid is obtained. The filtrate is reheated to boiling and absolute ethanol is added until a solid starts to precipitate. Cooling gives more solid. These two solids are combined, taken up in hot water, treated with charcoal and filtered. The filtrate is reheated and absolute ethanol is added until a solid begins to form. Cooling gives a solid, 4,4'4'',4'''-{carbonylbis[imino-5,1,3-benzenetriylbis(carbonylimino)]}-2,7-naphthalenedisulfonic acid] octasodium salt.

EXAMPLE 10

3,3'-[(5-Nitro-3,1-phenylene)bis(carbonylimino)]bis[2,7-naphthalenedisulfonic acid] tetrasodium salt A 6.5 g portion of 3-amino-2,7-naphthalenedisulfonic acid monosodium salt is suspended in 100 ml of water and the pH is adjusted to 7.5-8.0 giving a solution. A 1.82 g portion of sodium acetate is added and dissolved and 2.75 g of 5-nitro-1,3-benzenedicarbonylchloride is added. A 100 ml portion of water is added to maintain solution and the reaction is allowed to stand overnight. The mixture is treated with activated carbon and concentrated to about 50 ml on a rotary evaporator. The solid which forms is redissolved by heating on a steam bath. Cooling produces crystals which are dried overnight in an Abderhalden under high vacuum and refluxing toluene to give 3,3'-[(5-nitro-1,3-phenylene)bis(carbonylimino)]bis[2,7-naphthalenedisulfonic acid] tetrasodium salt.

EXAMPLE 11

3,3'-[(5-Amino-1,3-phenylene)bis(carbonylimino)]-bis[2,7-naphthalenedisulfonic acid] tetrasodium salt A mixture of 4.35 g of 3,3'-[(5-nitro-1,3-phenylene)-bis(carbonylimino)]bis[2,7-naphthalenedisulfonic acid] tetrasodium salt in 100 ml of water is heated to 57° C. A 2.07 g portion of sodium sulfide nonahydrate is added and the reaction is allowed to cool. The reaction is reheated to 67° C. and allowed to cool. The mixture is filtered and the filtrate is acidified to pH 4 using acetic acid. The mixture is heated and then filtered with added diatomaceous earth. Upon cooling the filtrate yields a solid which is filtered, washed with 50% ethanol, absolute ethanol and finally with ether giving 3,3'-[(5-amino-1,3-phenylene)bis(carbonylimino)]bis[2,7-naphthalenedisulfonic acid] tetrasodium salt.

EXAMPLE 12

4,4'-[5-Nitro-1,3-phenylenebis(carbonylimino)]bis[5-hydroxy)-2,7-naphthalenedisulfonic acid] tetrasodium salt A 100 g portion of 4-amino-5-hydroxy-2,7-naphthalenedisulfonic acid is recrystallized from water, washed with 50% ethanol, absolute ethanol and ether and dried in vacuo. A 35.9 g portion is suspended in 200 ml of water and the pH is adjusted to 7.0. A reaction flask is flushed with argon and the charged with the above suspension. A 9.05 g portion of sodium acetate is added followed by 13.15 g of 5-nitro-1,3-benzenedicarbonylchloride and the mixture is stirred for 3 hours. The solid is filtered, washed with 100 ml of 50% aqueous ethanol, two portions of absolute ethanol and finally two portions of ether and dried.

EXAMPLE 13

3,3',3'',3'''-[Carbonylbis[imino-5,1,3-benzenetriylbis(carbonylimino)]tetrakis[2,7-naphthalenedisulfonic acid] octasodium salt A 17.66 g portion of 3,3'-[(5-amino-1,3-phenylene)-bis(carbonylimino)]bis[2,7-naphthalenedisulfonic acid] tetrasodium salt is suspended in 300 ml of water and 8.95 g of sodium carbonate is added. Phosgene is added to the reaction mixture until it becomes acidic. The mixture is then made basic with 5N sodium hydroxide. The solid is filtered, recrystallized from water, washed with two 20 ml portions of 50% aqueous ethanol, two portions of absolute ethanol, two portions of ether and dried in vacuo giving the title compound.

EXAMPLE 14

6,6'-[5-Nitro-1,3-phenylenebiscarbonylimino)]bis[1,3-naphthalenedisulfonic acid] tetrasodium salt An 18.18 g portion of 6-amino-1,3-naphthalenedisulfonic acid is suspended in 200 ml of water and the pH is adjusted to 7.0 giving a solution. A 5.6 g portion of sodium acetate is dissolved in this solution and 8.18 g of 5-nitro-1,3-benzenedicarbonyl dichloride is added. The mixture is stirred for one hour, filtered and the filtrate is treated with activated carbon. The filtrate is reduced to a low volume on a rotary evaporator producing crystals. The crystals are recrystallized from water giving 6,6'-[5-nitro-1,3-phenylenebis(carbonylimino)]bis[1,3-naphthalenedisulfonic acid] tetrasodium salt.

EXAMPLE 15

4,4',4'',4'''-[Carbonylbis[imino-5,1,3-benzenetriylbis(carbonylimino)]]tetrakis[5-hydroxy-2,7-naphthalenedisulfonic acid] octasodium salt A 31.53 g portion of 4,4'-[5-nitro-1,3-phenylenebis(carbonylimino)]bis[5-hydroxy-2,7-naphthalenedisulfonic acid] tetrasodium salt is suspended in 200 ml of water and heated to 66° C. A 24.08 g portion of sodium sulfide is added and the temperature raised to 69° C. The mixture is twice cooled to 35° C. and then heated to 70°–75° C. After cooling the solution is acidified with 10 ml of acetic acid to pH 5. The resulting solid is filtered slowly, washed with three 150 ml portions of absolute ethanol, then with three portions of ether and dried in vacuo.

A 27.32 g portion of the above material and 14.1 g of sodium carbonate are added to 400 ml of water. Phosgene is bubbled into the mixture. A precipitate forms which is filtered, washed with two 100 ml portions of 50% aqueous ethanol, absolute ethanol and finally with three portions of ether and dried in vacuo overnight.

A 16.09 g portion of the above product is suspended in 200 ml of water and 8 ml of 10N sodium hydroxide is added producing a solution. The solution is phosgenated. An additional 8 ml of 10N sodium hydroxide is added to prevent precipitation and phosgenation is continued until the reaction becomes very acidic. The resulting solid is filtered, recrystallized from water and washed with two 50 ml portions of 50% aqueous ethanol, two 50 ml portions of absolute ethanol and three portions of ether. The product is dried in vacuo and then overnight over refluxing toluene under high vacuum in an Abderhalden giving the title compound.

EXAMPLE 16

Preparation of Compressed Tablet

| Ingredient | mg/Tablet |
|---|---|
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 17

Preparation of Compressed Tablet — Sustained Action

| Ingredient | mg/Tablet |
|---|---|
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 18

Preparation of Hard Shell Capsule

| Ingredient | mg/Capsule |
|---|---|
| Active Compound | 0.5–500 |
| Lactose, Spray Dried | qs |
| Magnesium Stearate | 1–10 |

EXAMPLE 19

Preparation of Oral Liquid (Syrup)

| Ingredient | % W/V |
|---|---|
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 20

Preparation of Oral Liquid (Elixir)

| Ingredient | % W/V |
|---|---|
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 21

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 22

Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 23

Preparation of Injectable Oil

| Ingredient | % W/V |
|---|---|
| Active Compound | 0.05–5 |
| Benzyl Alcohol | 0.5 |
| Sesame Oil qs ad | 100.0 |

EXAMPLE 24

Preparation of Intra-Articular Product

| Ingredient | Amount |
| --- | --- |
| Active Compound | 2-20 mg |
| NaCl (physiological saline) | 0.9% |
| Benzyl Alcohol | 0.9% |
| Sodium Carboxymethylcellulose | 1-5% |
| pH adjusted to 5.0-7.5 | |
| Water for Injection qs ad | 100% |

EXAMPLE 25

Preparation of Injectable Depo Suspension

| Ingredient | % W/V |
| --- | --- |
| Active Compound | 0.05-5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6-8 | qs |
| Water for Injection qs ad | 100.0 |

The compounds of the present invention may be administered internally, e.g., orally, intra-articularly or parenterally, e.g., intra-articular, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, the intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohols, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test, Code 026 (C1 inhibitor) — This test measures the ability of activated human C1 to destroy fluid phase human C2 in the presence of C4 and appropriate dilutions of the test compound. An active inhibitor protects C2 from C1 and C4; (ii) Test, Code 035 (C3-C9 inhibitor) — This test determines the ability of the late components of human complement (C3-C9) to lyse EAC 142 in the presence of appropriate dilutions of the test compound. An active inhibitor protects EAC 142 from lysis by human C3-C9; (iii) Test, Code 036 (C-Shunt inhibitor) — In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test — Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test — Lethal shock is produced in guinea pigs by an i.v. injection of anti-Forssman antiserum and the harmonic mean death time of treated guinea pigs is compared with that of simultaneous controls; (vi) Complement Level Reduction Test — In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7–8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests, code 026, 035, 036 Cap 50, % inhibition and Forssman shock. Table I shows that the compounds of the invention possess highly significant in situ and in vivo, complement inhibiting activity in warm-blooded animals.

tion is diluted with absolute ethanol and filtered to give the title compound.

EXAMPLE 27

6,6′,6″,6‴-[Carbonylbis[imino-5,1,3-benzenetriylbis(carbonylimino)]]tetrakis[1,3-naphthalenedisulfonic acid] octasodium salt A solution of the preceeding amino compound from Example 26 and excess sodium carbonate in water is treated with phosgene as in Example 12 to give the title product.

We claim:

1. A compound of the formula:

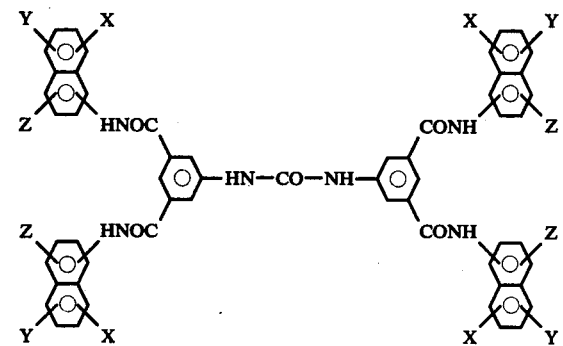

wherein X, Y and Z are selected from the group consisting of hydrogen, hydroxy, and —SO$_3$R$_1$, wherein R$_1$ is

TABLE I
BIOLOGICAL ACTIVITIES

| | | | | | In Vivo Activity (Guinea Pig) % Inhibition | | | | | | | |
|---|---|---|---|---|---|---|---|---|---|---|---|---|
| | | | | | Intraperitoneal Time(Hours) | | | | Intravenous Time(Hours) | | | |
| Compound | Cl 026* Wells | C-Late 035* Wells | Shunt Inhibition 036* Wells | Cap 50* | 30 | 60 | 120 | HCT | 2 | 30 | 120 | HCT |
| 8,8′,8″,8‴-[Carbonylbis[imino-5,1,3-benzenetriylbis(carbonylimino)]]tetrakis[1,3,6-naphthalenetrisulfonic acid] dodecasodium salt | +9 | +3 | +5 | 76 | −88 | −85 | −92 | −8(5/6) | −98 | −97 | −89 | −9(5/6) |
| 4,4′,4″,4‴-[Carbonylbis[imino-5,1,3-benzenetriylbis(carbonylimino)]]tetrakis[2,7-naphthalenedisulfonic acid] octasodium salt | +5,+6 | N**,+1 | +3 | 166,156 | | | | | | | | |
| 4,4′,4″,4‴-[Carbonylbis[imino-5,1,3-benzenetriylbis(carbonylimino)]]tetrakis[5-hydroxy-2,7-naphthalenedisulfonic acid] octasodium salt | +5,+6 | +2,+1 | +1 | 138 | −69 | −92 | −98 | +6(5/5) | | | | |
| 8,8′,8″,8‴-[Carbonylbis[imino-5,1,3-benzenetriylbis(carbonylimino)]]tetrakis[1-3,5-naphthalenesulfonic acid] dodecasodium salt | +7,+8 | +4,+2 | +6, +5 | 45 | −98 | −98 | −99 | −3(5/5) | | | | |

*Code designations for tests employed
**N means inactive, O Wells

EXAMPLE 26

6,6′-[5-Amino-1,3-phenylenebis(carbonylimino)]bis[1,3-naphthalenedisulfonic acid] tetrasodium salt To a solution of 13.49 g of 6,6′-[5-nitro-1,3-phenylenebis(carbonylimino)]bis[1,3-naphthalenedisulfonic acid] tetrasodium salt in 200 ml of water at 65° C. is added 6.42 g of sodium sulfide nonahydrate. After heating on the steam bath at 70° to 75° C. the solution is cooled, acidified with acetic acid and filtered. The filtrate is adjusted to pH 6 with 5N sodium hydroxide solution and concentrated to small volume. The solution selected from the group consisting of hydrogen, alkali metal and alkali earth methal; and with the proviso that when X, Y or Z is hydrogen or hydroxy, then the remaining two substituents must be —SO$_3$R$_1$.

2. The compound according to claim 1, 8,8′,8″8‴-[carbonylbis[imino-5,1,3-benzenetriylbis(carbonylimino)]]tetrakis[1,3,6-naphthalenetrisulfonic acid].

3. The compound according to claim 1, 8,8′,8″8‴-[carbonylbis[imino-5,1,3-benzenetriylbis(carbonylimino)]]tetrakis[1,3,6-naphthalenetrisulfonic acid] dodecasodium salt.

4. The compound according to claim 1, 8,8',8'',8'''-[carbonylbis[imino-5,1,3-benzenetriylbis(carbonylimino)]]tetrakis[1,3,5-naphthalenetrisulfonic acid] dodecasodium salt.

5. The compound according to claim 1, 4,4',4'',4'''-carbonylbis[imino-5,1,3-benzenetriylbis(carbonylimino)]]tetrakis[2,7-naphthalenesulfonic acid] octasodium salt.

6. The compound according to claim 1, 3,3',3'',3'''-[carbonylbis[imino-5,1,3-benzenetriylbis(carbonylimino)]]tetrakis[2,7-naphthalenedisulfonic acid] octasodium salt.

7. The compound according to claim 1, 4,4',4'',4'''-[carbonylbis[imino-5,1,3-benzenetriylbis(carbonylimino)]]tetrakis[(5-hydroxy-2,7-naphthalenedisulfonic acid]octasodium salt.

8. The compound according to claim 1, 6,6',6'',6'''-[carbonylbis[imino-5,1,3-benzenetriylbis(carbonylimino)]]tetrakis[1,3-naphthalenedisulfonic acid]octasodium salt.

* * * * *